United States Patent
Yi et al.

(10) Patent No.: US 10,353,165 B2
(45) Date of Patent: *Jul. 16, 2019

(54) STAND EQUIPPED WITH COUNTERBALANCE UNIT

(71) Applicants: KOH YOUNG TECHNOLOGY INC., Seoul (KR); INDUSTRY-UNIVERSITY COOPERATION FOUNDATION HANYANG UNIVERSITY ERICA CAMPUS, Ansan-si, Gyeonggi-do (KR)

(72) Inventors: Byung-Ju Yi, Bucheon-si (KR); Jong-Tae Seo, Ansan-si (KR)

(73) Assignees: KOH YOUNG TECHNOLOGY INC., Seoul (KR); INDUSTRY-UNIVERSITY COOPERATION FOUNDATION HANYANG UNIVERSITY ERICA CAMPUS, Ansan-si, Gyeonggi-Do (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/634,120

(22) Filed: Jun. 27, 2017

(65) Prior Publication Data

US 2017/0299838 A1    Oct. 19, 2017

Related U.S. Application Data

(63) Continuation-in-part of application No. 14/372,882, filed as application No. PCT/KR2014/004649 on May 23, 2014.

(30) Foreign Application Priority Data

May 24, 2013  (KR) .................. 10-2013-0059337
May 22, 2014  (KR) .................. 10-2014-0061915

(51) Int. Cl.
*G02B 7/00*        (2006.01)
*G02B 21/24*       (2006.01)
(Continued)

(52) U.S. Cl.
CPC .............. *G02B 7/001* (2013.01); *A61B 90/25* (2016.02); *A61B 90/50* (2016.02); *F16M 11/06* (2013.01);
(Continued)

(58) Field of Classification Search
CPC .... G02B 7/001; F16M 11/2007; F16M 11/38; F16M 2200/063; A61B 90/50;
(Continued)

(56) References Cited

U.S. PATENT DOCUMENTS 13,739 A * 10/1855 Hunter .................... F21V 21/38
                                                    248/281.11
142,263 A * 8/1873 Morrison ............... F16M 11/04
                                                    248/281.11
(Continued)

FOREIGN PATENT DOCUMENTS

CN    2109175      7/1992
CN    2452453      10/2001
(Continued)

OTHER PUBLICATIONS

International Search Report for International Application No. PCT/KR2014/004649, dated Aug. 22, 2014.
(Continued)

*Primary Examiner* — Kimberly T Wood
(74) *Attorney, Agent, or Firm* — Kile Park Reed & Houtteman PLLC

(57) ABSTRACT

A stand includes first to fourth links, first to fourth joints, a front link, first to fifth extension links, and first to fourth extension joints. The first to fourth links are arranged in a
(Continued)

parallelogram configuration, wherein the first and third links are arranged on opposite sides and the second and fourth joints are arranged in a diagonal direction. The front link extends from the first link. The first extension link is rotatably connected to the second joint. The second extension link is rotatably connected to the first extension joint. The third extension link is rotatably connected to the second extension joint. The fourth extension link is arranged between the third extension joint and the fourth extension joint. The fifth extension link is arranged between the first joint and the second extension joint. The first, fourth, and fifth extension links are in parallel with one another.

6 Claims, 9 Drawing Sheets

(51) Int. Cl.
```
F16M 11/12      (2006.01)
A61B 90/50      (2016.01)
F16M 11/06      (2006.01)
F16M 11/20      (2006.01)
F16M 11/38      (2006.01)
A61B 90/25      (2016.01)
A61G 12/00      (2006.01)
```
(52) U.S. Cl.
CPC ....... *F16M 11/121* (2013.01); *F16M 11/2007* (2013.01); *F16M 11/38* (2013.01); *G02B 21/24* (2013.01); *A61B 2090/504* (2016.02); *A61B 2090/506* (2016.02); *A61G 12/002* (2013.01); *F16M 2200/041* (2013.01); *F16M 2200/047* (2013.01); *F16M 2200/063* (2013.01); *F16M 2200/066* (2013.01)

(58) Field of Classification Search
CPC ...... A61B 2090/5025; A61B 2090/504; A61B 2090/506
USPC ................ 248/123.2, 278.1, 280.11, 281.11; 359/384
See application file for complete search history.

(56) References Cited

U.S. PATENT DOCUMENTS

| | | | | |
|---|---|---|---|---|
| 1,070,524 A | * | 8/1913 | Pieper | F16M 11/04 248/281.11 |
| 1,178,058 A | * | 4/1916 | Cruse | F16M 11/12 248/278.1 |
| 1,189,754 A | * | 7/1916 | Trenaman | F16M 11/04 248/281.11 |
| 4,339,100 A | | 7/1982 | Heller et al. | |
| 5,173,802 A | | 12/1992 | Heller | |
| 5,186,422 A | | 2/1993 | Nakamura | |
| 5,480,114 A | | 1/1996 | Nakamura | |
| 5,528,417 A | | 6/1996 | Nakamura | |
| 5,812,301 A | | 9/1998 | Nakamura | |
| 5,818,638 A | | 10/1998 | Nakamura | |
| 5,825,536 A | | 10/1998 | Yasunaga et al. | |
| 6,105,909 A | | 8/2000 | Wirth et al. | |
| 7,018,386 B2 | | 3/2006 | Nakamura | |
| 7,461,824 B2 | | 12/2008 | Poxleitner et al. | |
| 7,942,378 B2 | | 5/2011 | Nakamura | |
| 8,038,108 B2 | | 10/2011 | Yasunaga et al. | |
| 9,364,290 B2 | * | 6/2016 | Yi | A61B 90/30 |
| 2003/0151805 A1 | | 8/2003 | Schmidt | |
| 2004/0172012 A1 | | 9/2004 | Otsuka et al. | |
| 2004/0190131 A1 | | 9/2004 | Brenner et al. | |
| 2008/0237413 A1 | | 10/2008 | Hammer | |
| 2013/0140412 A1 | | 6/2013 | Hirose | |

FOREIGN PATENT DOCUMENTS

| | | |
|---|---|---|
| DE | 197 42 051 | 3/1999 |
| DE | 93 21 575 | 1/2000 |
| EP | 0 023 003 | 1/1981 |
| EP | 0 419 070 | 3/1991 |
| EP | 0 609 085 | 8/1994 |
| JP | 6-197912 | 7/1994 |
| JP | 6-217993 | 8/1994 |
| JP | 7-227791 | 8/1995 |
| JP | 10-272143 | 10/1998 |
| JP | 11-28216 | 2/1999 |
| JP | 11-153293 | 6/1999 |
| JP | 2009-514633 | 4/2009 |
| WO | 2010/085901 | 8/2010 |
| WO | 2012/117922 | 9/2012 |

OTHER PUBLICATIONS

Written Opinion with English Translation for International Application No. PCT/KR2014/004649, dated Aug. 22, 2014.
Naoyuki Takesue, "Gravity Compensation Mechanisms for Energy-Saving and Safety", JRSJ, vol. 29, No. 6, pp. 508-511, 2011.
Japanese Notice of Allowance with English Translation for Japanese Patent Application 2017-021023, dated Feb. 5, 2019.
Chinese Office Action with English Translation for Chinese Patent Application 201710301720, dated Mar. 4, 2019.

* cited by examiner

STAND EQUIPPED WITH COUNTERBALANCE UNIT

CROSS-REFERENCE TO RELATED APPLICATIONS

This application is a continuation-in-part of U.S. application Ser. No. 14/372,882, filed on Jul. 17, 2014 (now pending), which is a national stage filing under 35 U.S.C § 371 of International Application No. PCT/KR2014/004649 filed on May 23, 2014, which claims the benefits of Korean Patent Application No. 10-2013-0059337 filed on May 24, 2013 and Korean Patent Application No. 10-2014-0061915 filed on May 22, 2014, the entire contents of each of which are incorporated herein by reference.

TECHNICAL FIELD

The present disclosure relates to a stand equipped with a counterbalance unit, more particularly, a stand equipped with a counterbalance unit wherein a medical apparatus such as a microscope and a surgical end effector can be installed and moved to a desired position.

BACKGROUND

Microsurgery, in which a medical surgical microscope is used to observe affected parts while performing surgery, has been studied and introduced in the surgical operation field.

In such microsurgery, a stand is needed to install weighty objects, i.e., a surgical microscope with its attached devices; place them in a desired space; then maintain their position.

Generally, in such a stand, the middle part of a link unit using a parallel link is rotatably connected to a holding unit, while a surgical microscope is installed at one end of the link unit and has a balanced structure having a counterweight which is installed at the other one end of the surgical microscope to counterbalance a weight of the surgical microscope around a rotation point.

Since accessories, such as an assistant scope or a video camera, etc., are installed in the surgical microscope, an overall balance adjustment operation is carried out by changing a position of the counterweight according to its weight such that the surgical microscope and the counterweight are balanced.

However, in case when the surgical microscope and its attached devices remain in the desired position, their vertical balance needs to be maintained. However, a conventional stand has difficulties in controlling the vertical balance since the total weight of the surgical microscope is inconsistent due to the presence and absence of various attachments.

SUMMARY

Embodiments of the present disclosure are provided to solve the problem stated above. Embodiments of the present disclosure provide a stand equipped with a counterbalance unit capable of maintaining a reliable and efficient counterbalance regardless of positions of a medical apparatus.

Embodiments of the present disclosure provide a stand equipped with a replaceable counterweight based on the amount of a torque in joints caused by a medical apparatus, and a counterbalance unit capable of adjusting the length of a balance link.

Embodiments of the present disclosure provide a stand equipped with a counterbalance unit capable of adding degree of freedom easily.

According to one exemplary embodiment, a stand equipped with a counterbalance unit includes: four links arranged in a square configuration; four joints that are connected to each connection part of the four links respectively and enable the links to be mutually rotatable; a front link, to a tip of which a medical apparatus is mounted, extended from an end of any one of the four links; and a counterbalance unit connected to a joint that is diagonally located from a joint from where the front link is extended.

The stand equipped with a counterbalance unit according to an embodiment of the present disclosure can obtain a large torque compensation effect with small weight by optimizing the mounting position of counterbalance.

In addition, even when a number of medical apparatus such as a microscope and the like are used, because of a replaceable counterweight based on the amount of the torque in joints caused by the medical apparatus and a counterbalance unit capable of adjusting the length of a balance link, a reliable and efficient counterbalance can be maintained.

Moreover, multiple extension link members can be installed according to the purpose of a user, thus increase the degree of freedom of the movement of the medical apparatus.

DETAILED DESCRIPTION

Hereinafter, more detailed description of a stand equipped with a counterbalance unit according to embodiments of the present disclosure is provided with reference to appended drawings.

Figure 1:
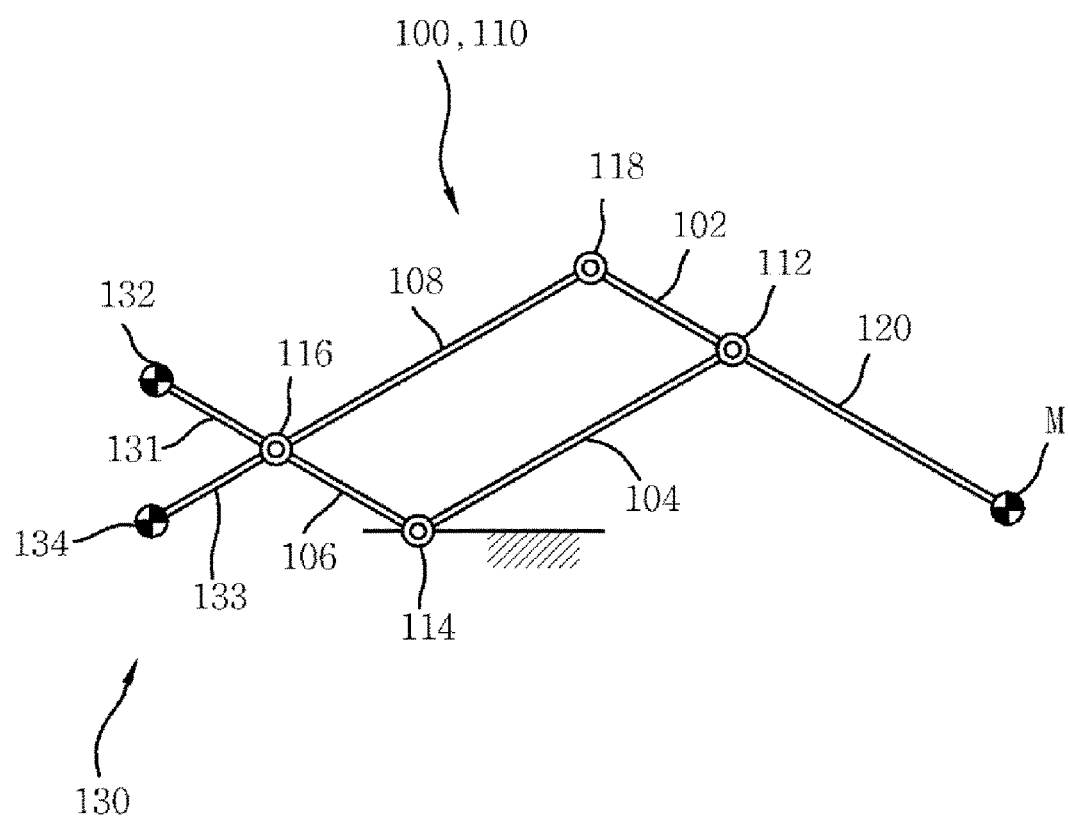
FIG. 1 is a schematic diagram illustrating a stand equipped with a counterbalance unit according to one embodiment of the present disclosure.
Figure 2A:
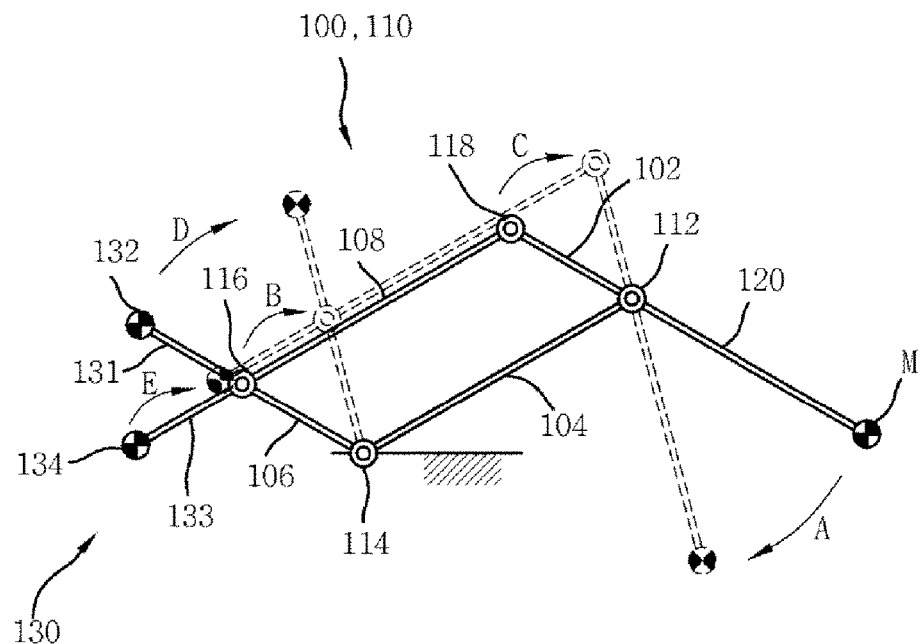
FIGS. 2A and 2B are schematic diagrams illustrating the stand shown in FIG. 1 in operation modes.
Figure 2B:
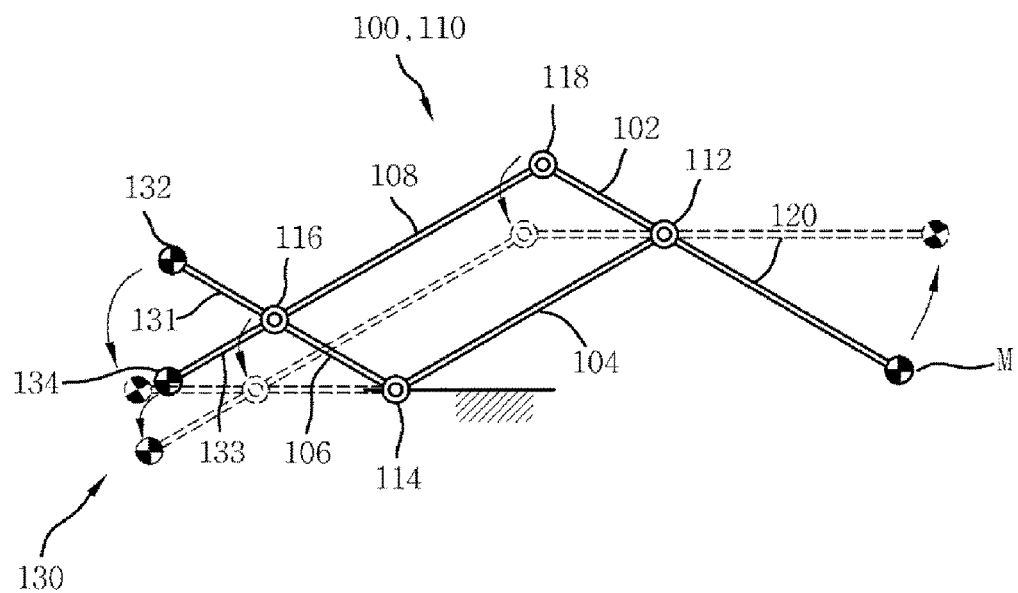
Figure 3:
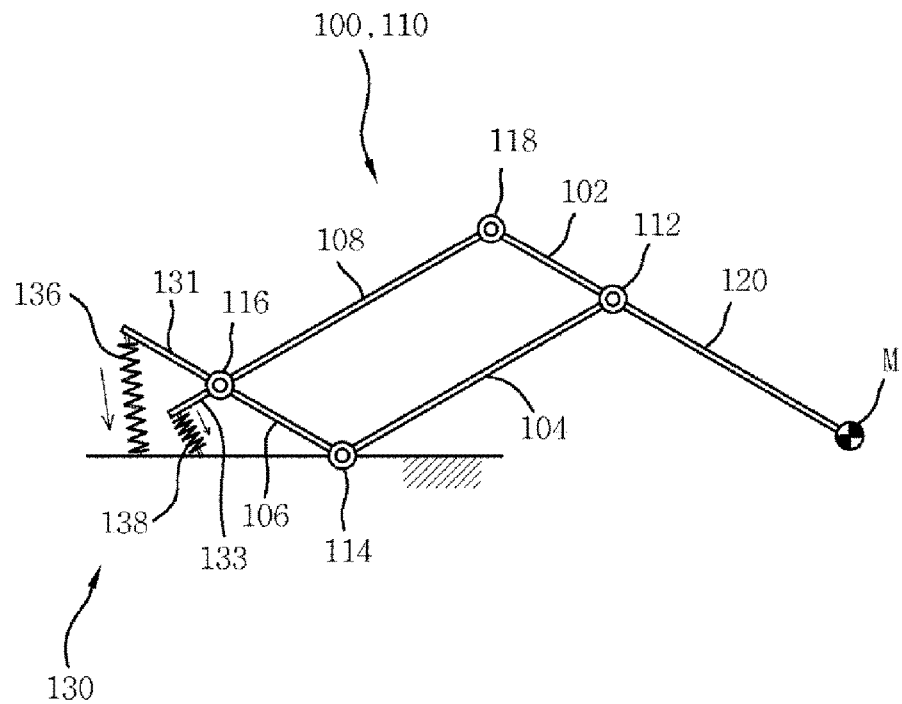
FIG. 3 is a schematic diagram illustrating an embodiment of a counterbalance unit.

Embodiments of the present disclosure are related to a stand equipped with a counterbalance unit. FIG. 1 is a schematic diagram illustrating a stand equipped with a counterbalance unit according to one embodiment of the present disclosure. FIGS. 2A and 2B are schematic diagrams illustrating the stand shown FIG. 1 in operation modes. FIG. 3 is a schematic diagram illustrating an embodiment of a counterbalance unit.

A stand equipped with a counterbalance unit according to one embodiment of the present disclosure includes: four links 100 arranged in a square configuration; four joints 110 that are connected to each connection part of the four links 100 respectively and enable these links 100 to be mutually rotatable; a front link 120 that is extended from an end of any one of the four links 100 with a medical apparatus M being mounted to a tip of the front link; a counterbalance unit 130 connected to a joint 110 that is diagonally located from the joint 110 from which the front link 120 is extended.

Each component is described in more details as follows.

Joints 110 include first, second, third and fourth joints 112, 114, 116, 118 and are connected to each connection part of the four links 100 respectively so that the links 100 are mutually rotatable.

The links 100 include a first link 102 whose both ends are connected to the first and fourth joints 112, 118; a third link 106 whose both ends are connected to the second and third joints 114, 116 and placed (or arranged) on the opposite side of the first link 102; a second link 104 whose both ends are connected to the first and second joints 112, 114; and a fourth link 108 whose both ends are connected to the third and fourth joints 116, 118 and placed on the opposite side of the second link 104. The links 100 are arranged in a square configuration. By way of example, the links 100 are arranged in a parallelogram configuration as illustrated in FIG. 1. The description hereinafter relates to an embodiment in which the links 100 are arranged in a parallelogram configuration. In case where the links 100 are not formed in a parallelogram configuration, parallel can be understood as opposite.

Both ends of the first link 102 are connected to the first and fourth joints 112, 118, while the third link 106 is located in parallel to the first link 102 and both ends of the third link 106 are connected to the second and third joints 114, 116. In addition, both ends of the second link 104 are connected to the first and second joints 112, 114, and both ends of the fourth link 108 are connected to the second and third joints 114, 116. The second link 104 and the fourth link 108 are parallel with each other. Accordingly, the first, second, third and fourth links 102, 104, 106, 108 are mutually rotatable and thus a medical apparatus M which will be described below has a degree of freedom.

Further, at least any one of the four joints 110 is fixed to and supported by a holding unit (not shown). By way of example, in case of an embodiment of the present disclosure, the second joint 114 is fixed to and supported by the holding unit.

A front link 120 is extended from an end of any one link of the four links 100 and the medical apparatus M is mounted at a tip of the front link. The front link is interlocked to the movement of the links 100 to move the medical apparatus M. In the embodiment of the present disclosure, the front link 120 is extended from an end of the first link 102 as illustrated in FIG. 1, and the first joint 112 is connected between the first link 102 and the front link 120.

By way of example, the counterbalance unit 130 is connected to the joint 110 which is placed (or arranged) in a diagonal direction from the joint 110 that is located at the extension part from which the front link 120 is extended. The counterbalance unit functions to counterbalance the medical apparatus M. That is, according to the embodiment of the links 100, as illustrated in FIG. 1, the first joint 112 is placed at the extension part from which the front link 120 is extended, and the third joint 116 is positioned in the diagonal direction from the first joint 112, thus the counterbalance unit 130 is connected to the third joint 116.

The counterbalance unit 130 in the present disclosure can use weighters and springs to balance against the front link 120 with the medical apparatus M. Hereinafter, the description of the case using the weighters will be made first.

The counterbalance unit 130 includes first and second balancing links 131, 133 extended from the two links 100, i.e., the third and fourth links 106, 108 connected to the third joint 116; and first and second counterweights 132, 134 respectively mounted at the tips of the first and second balancing links 131, 133.

The first and second counterweights 132, 134 are placed on the opposite side of the medical apparatus M, centering on the second joint 114, to maintain balance. When the medical apparatus M moves in the direction opposite to gravity, the first and second counterweights 132, 134 move in the direction of gravitational force, thus compensating the torque in joints caused by the medical apparatus.

The counterbalance unit 130 may not be connected to the second joint 114 that functions as the central axis. As illustrated in FIG. 1, the counterbalance unit 130 may be connected to the third joint 116. Thus, the effective distance to the central axis (the distance between the central axis and the gravity vector acting on the counterweights) is maximized in most movements of the links 100, and the torque in joints generated by the medical apparatus can be compensated in full.

Further, the length of the first and second balancing links 131, 133 is adjustable, and each of the first and second counterweights 132, 134 is removably installed on the first and second balancing links 131, 133 respectively, thus the compensated torque in joints can be controlled in accordance with the length of the front link 120 or the weight of a medical apparatus M.

The counterbalance unit 130 in another embodiment includes the first and second balancing links 131, 133 extended from the third and fourth links 106, 108; and first and second counter springs 136, 138 attached to the tips of the first and second balancing links 131, 133 respectively.

The holding unit fixing the second joint 114 may be extended in parallel with the ground. As illustrated in FIG. 3, one end of the first counter spring 136 is connected to the tip of the first balancing link 131, while the other end of the first counter spring 136 is connected to the holding unit. In this case, the first counter spring 136 is a tension spring, and moves the first balancing link 131 in the gravitational direction, i.e. the direction of the arrow, thus compensating the torque in joints generated by the medical apparatus M. One end of the second counter spring 138 is connected to the tip of the second balancing link 133, while the other end of the second counter spring 138 is connected to the holding unit. The second counter spring 138 is also a tension spring and moves the second balancing link 133 in the direction of the arrow, thus compensating the torque in joints generated by the medical apparatus.

Also, when necessary, one end of the counter spring is connected to the third link 106 and the other end of the counter spring is connected to the holding unit.

Hereinafter, the operation mode of the stand equipped with a counterbalance unit according to the present disclosure will be described with reference to appended drawings.

Referring to FIG. 2A, when the medical apparatus M moves in the direction A complying with gravity, due to the structure of the links 100, each of the third and fourth joints 116, 118 moves in the direction B and C respectively, therefore, the first and second counterweights 132, 134 independently move in the direction D and E opposite to the direction of gravity. Consequently, the potential energy of the first and second counterweights 132, 134 increases, therefore, the medical apparatus M can move with less force when the medical apparatus M to returns to its original position or moves to other positions as illustrated in FIG. 2B.

Conversely, when the medical apparatus M moves in the direction opposite to gravity as illustrated in FIG. 2B, the links 100 function to the opposite direction from FIG. 2A, and thus the first and second counterweights 132, 134 are moved in the direction complying with gravity. Therefore, the potential energy is decreased and the medical apparatus M can be moved against gravity with little force.

Figure 4:
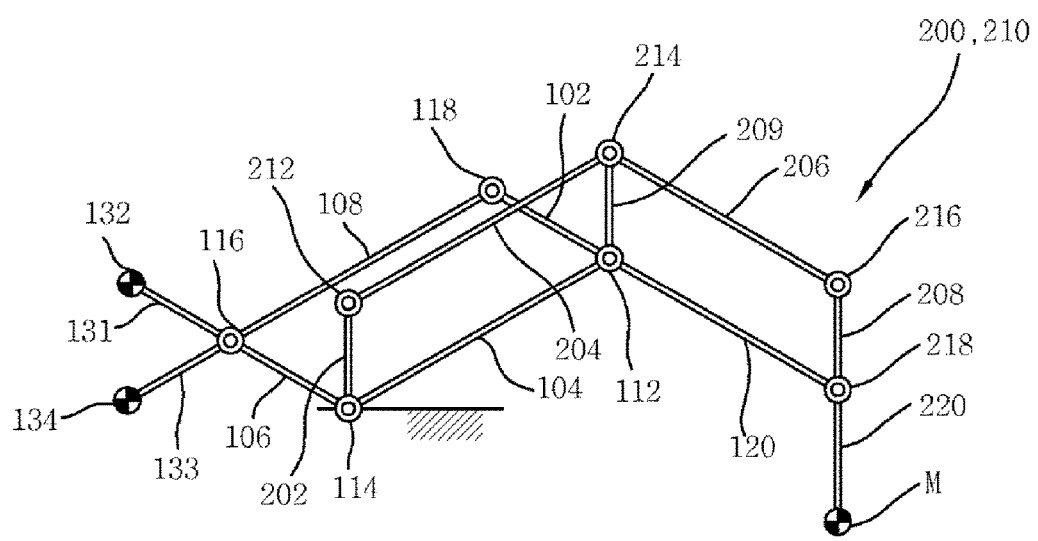
FIG. 4 is a schematic diagram illustrating a stand equipped with extension link members according to a further embodiment of the present disclosure.
Figure 5:
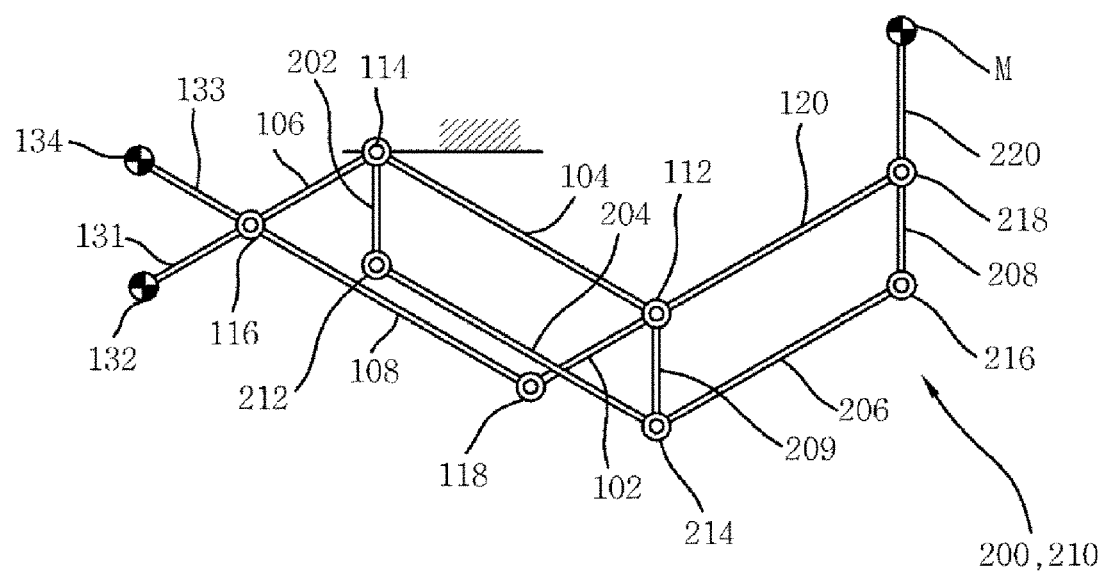
FIG. 5 is a schematic diagram illustrating a stand equipped with extension link members according to another embodiment of the present disclosure.
Figure 6A:
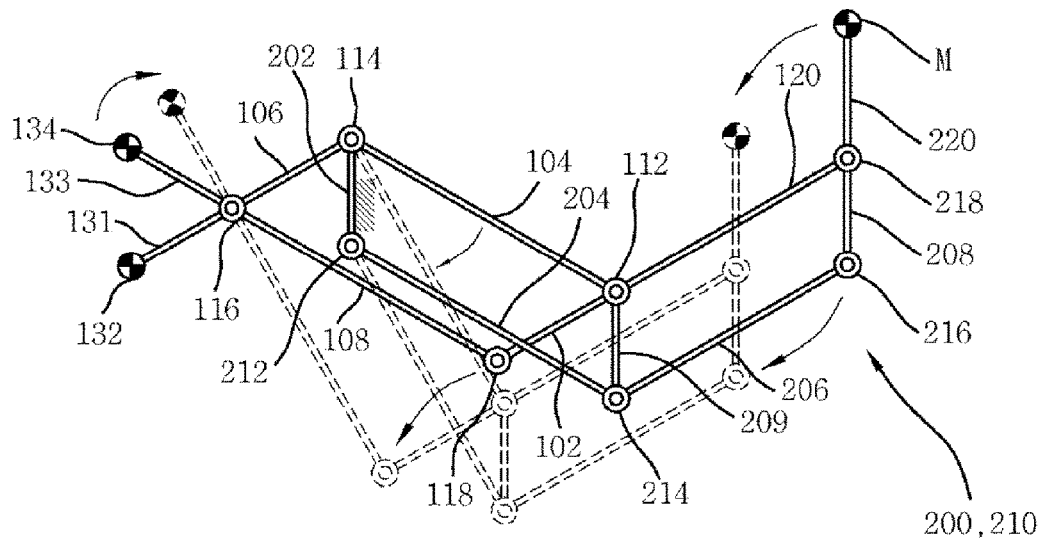
FIGS. 6A and 6B are schematic diagrams illustrating the stand shown in FIG. 5 in operation modes.
Figure 6B:
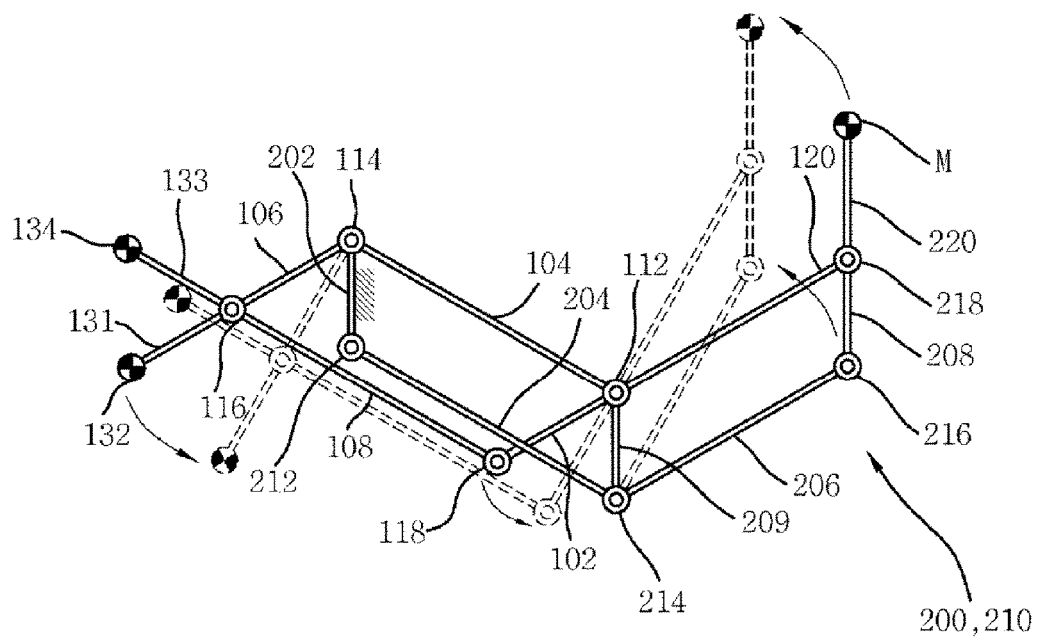

FIG. 4 is a schematic diagram illustrating a stand equipped with extension link members. FIG. 5 is a schematic diagram illustrating another embodiment of FIG. 4. FIGS. 6A and 6B are a schematic diagram illustrating the operation modes of FIG. 5.

The extension link members include extension links 200 connected to the links 100 and the front link 120; extension joints 210 connected to each connection part of the extension links 200 respectively and capable of mutually rotating the extension links 200; and an extension front link 220 extended from an end of the extension link 200 that is one of extension links 200 and connected to the front link 120, thereby functioning to increase the degree of freedom of the medical apparatus M.

The extension joints 210 include first, second, third and fourth extension joints 212, 214, 216, 218.

The extension links 200 are placed at the opposite side of the second link 104. The extension links 200 include: a second extension link 204 whose both ends are connected to the first and second extension joints 212, 214; a third extension link 206 placed at the opposite side of the front link 120, one end of the third extension link 206 being connected to the second extension joint 214 and the other end of the third extension link 206 being connected to the third extension joint 216; a first extension link 202 whose both ends are respectively connected to the second joint 114 and the first extension joint 212; a fourth extension link 208 whose one end is connected to the third extension joint 216 and whose the other end is connected to the fourth extension joint 218; and a fifth extension link 209 whose both ends are respectively connected to the first joint 112 and the second extension joint 214.

In the extension link members illustrated in FIG. 4, each of the second and third extension links 204, 206 is placed in parallel with the second link 104 and the front link 120 respectively, and one ends of the second and third extension links 204, 206 are connected to each other through the second extension joint 214. Further, the other end of the second extension link 204 is connected to the first extension joint 212 and the other end of the third extension link 206 is connected to the third extension joint 216. In addition, the both ends of the first extension link 202 are connected to the second joint 114 and the first extension joint 212, and the both ends of the fourth extension link 208 are connected to the third extension joint 216 and the fourth extension joint 218. Further, the both ends of the fifth extension link 209 are connected to the first joint 112 and the second extension joint 214. That is, the extension links 200 have the shape of two overlapped parallelograms and are extended from the second joint 114 that is the center point.

According to the embodiment, the first extension link 202 can be fixed perpendicularly to the installation surface in order to maintain an extension front link 220, which will be described below, to be vertical. In such a case, since the first extension link 202 and the fifth extension link 209 are always in parallel and the fifth extension link 209 and the fourth extension link 208 are always in parallel, the extension front link 220 extended from the fourth extension link 208 is likewise in parallel with the first extension link 202 all the time. Accordingly, in case where the medical apparatus M such as a microscope should always remain vertical, the medical apparatus M can always remain vertical by vertically fixing the first extension link 202.

The extension front link 220 is extended from the fourth extension link 208, and the medical apparatus M is mounted to the tip of the extension front link 220. After all, the extension links 200 are the supplementary means for connecting the extension front link 220 and the medical apparatus M is interlocked with the movement of the links 100 as well as the movement of the extension link members by the extension front link 220 to increase the degree of freedom.

Further, as illustrated in FIG. 5, the stand equipped with a counterbalance unit according to the present disclosure can be formed in the shape in which the top and the bottom of FIG. 4 are inverted. In this case, the medical apparatus M functions upwardly, and may be used as an objective lens of a microscope. Similarly, as illustrated in FIGS. 6A and 6B, the first extension link 202 can be fixed perpendicularly to the ground and the extension front link 220 can move while always remaining vertical.

Figure 7:
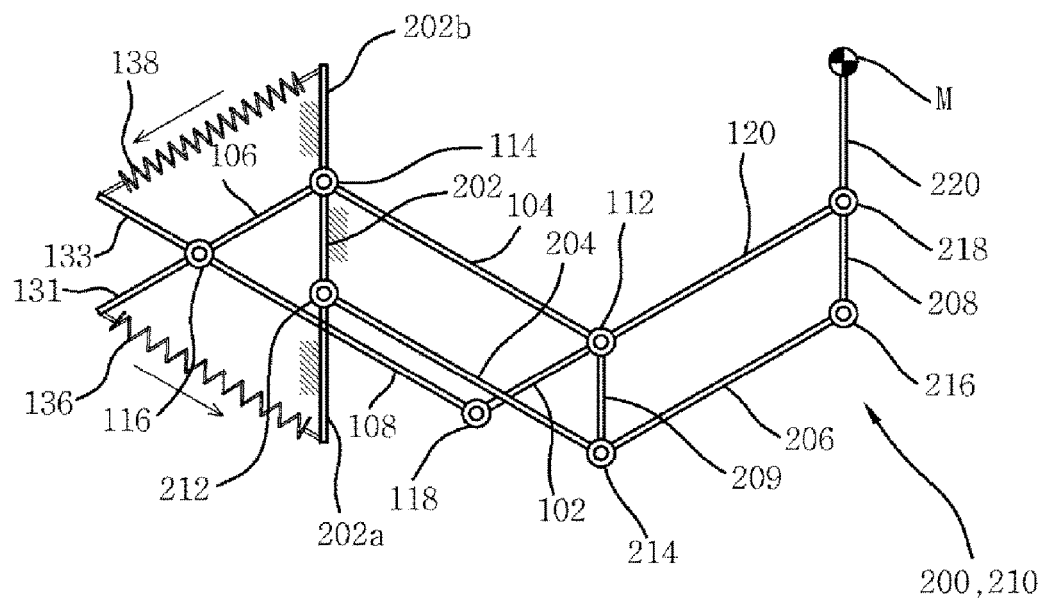
FIGS. 7 to 9 are schematic diagrams illustrating various embodiments of a counterbalance unit.
Figure 8:
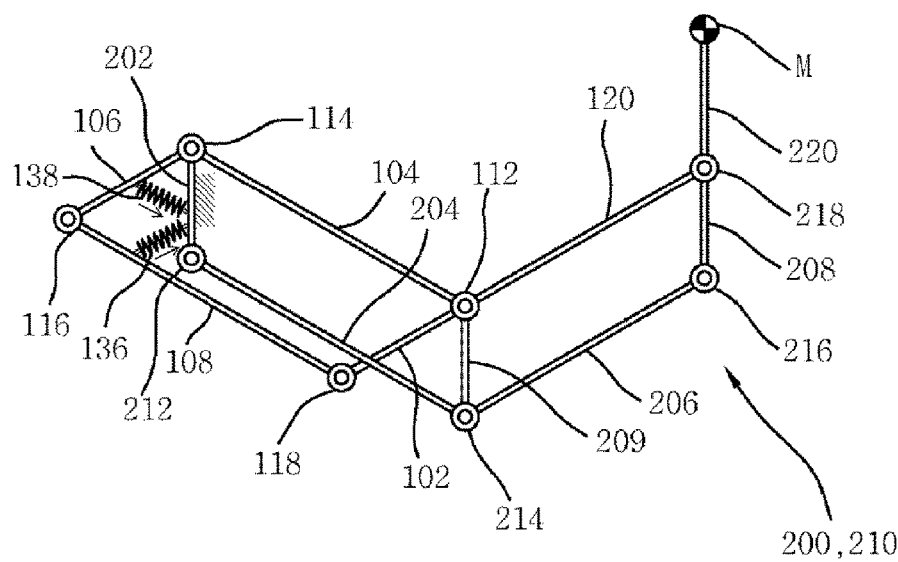
Figure 9:
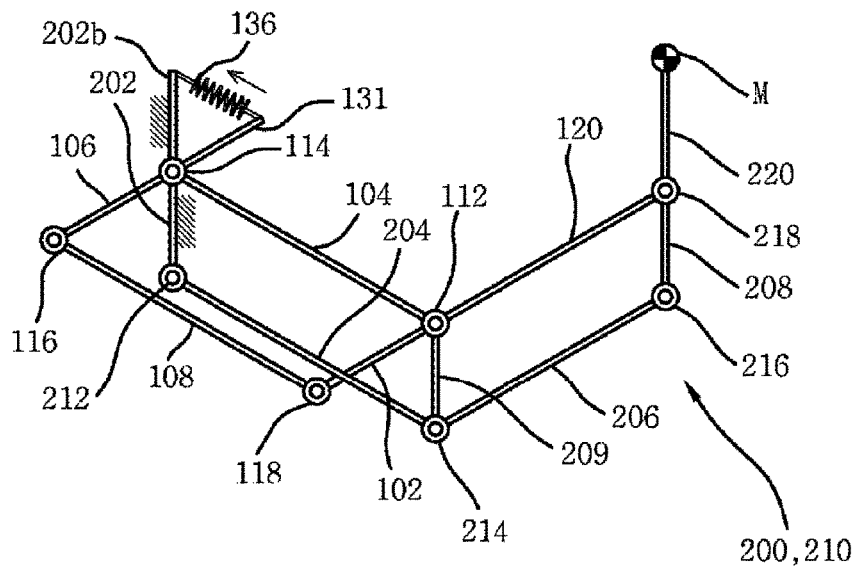

FIGS. 7 to 9 are schematic diagrams illustrating various embodiments of the counterbalance unit.

Hereinafter, embodiments of the stand equipped with extension link members, to which counter springs are applied, will be described with reference to the appended drawings.

First, referring to FIG. 7, the stand is provided with the first and second balancing links 131, 133 extended from the third and fourth links 106, 108; and first and the second auxiliary links 202*a*, 202*b* extended from the first extension link 202. The first and second auxiliary links 202*a*, 202*b* are fixed perpendicularly to the ground like the first extension link 202. And, one end of the first counter spring 136 is connected to the tip of the first balancing link 131, while the other end of the first counter spring 136 is connected to the first auxiliary link 202*a*. In this case, the first counter spring 136 is a tension spring and moves the first balancing link 131 in the gravitational direction, i.e. the direction of the arrow, to compensate the torque in joints generated by the medical apparatus M. One end of the second counter spring 138 is connected to the tip of the second balancing link 133, while the other end of the second counter spring 138 is connected to the second auxiliary link 202*b*. In this case, the second counter spring 138 is a compression spring and moves the second balancing link 133 in the direction of the arrow to compensate the torque in joints generated by the medical apparatus M.

Referring to FIG. 8 as another embodiment, one end of the first counter spring 136 is connected to the fourth link 108, while the other end of the first counter spring 136 is connected to the first extension link 202. One end of the second counter spring 138 is connected to the third link 106, while the other end of the second counter spring 138 is connected to the first extension link 202. The first and second counter springs 136, 138 are tension springs and each of the first and second counter springs 136, 138 moves the fourth link 108 and the third link 106 in the directions of the arrows respectively to compensate the torque in joints generated by the medical apparatus M.

Referring to FIG. 9 as a further embodiment, the second auxiliary link 202*b* is extended from the first extension link 202, and the first balancing link 131 is extended from the third link 106 connected to the second joint 114. One end of the first counter spring 136 is connected to the first balancing link 131, while the other end of the first counter spring 136 is connected to the second auxiliary link 202b. In this case, the first counter spring 136 is a tension spring, and moves the first balancing link 131 in the direction of the arrow to compensate the torque in joints generated by the medical apparatus M.

Thus, in case where the counter springs are applied to the stand equipped with extension link members, various embodiments can be made. For the greater variety of embodiments, the stand may be provided with the counter springs that are directly connected to the links 100 or the extension links 200. Further, when necessary, additional balancing links may be added to the stand.

Further, when necessary, more extension link members can be added to the stand. An additional link is connected to the second joint 114 supported by the holding unit, a link is connected in parallel with the second link 104, and links, each of which is in parallel with the front link 120 and the extension front link 220 respectively, are connected. Next, an additional front link is connected to the extension front link 220 and then the medical apparatus is mounted to the tip of the connected additional front link. In this way, N number of extension link members can be additionally mounted, variously setting the degree of freedom of the medical apparatus.

As the number of extension link members increases, the medical apparatus M gets further from the second joint 114 that is the center point of rotation, accordingly, the torque in joints generated by the medical apparatus M grows bigger. In order to maintain a stable counterbalance, the lengths of the first and second balancing links 131, 133 may increase in proportion to the growing number of the extension link members. For the efficient counter balance, the weight of the first and second counterweights 132, 134 as well as the lengths of the first and second balancing links 131, 133 may increase.

Figure 10:
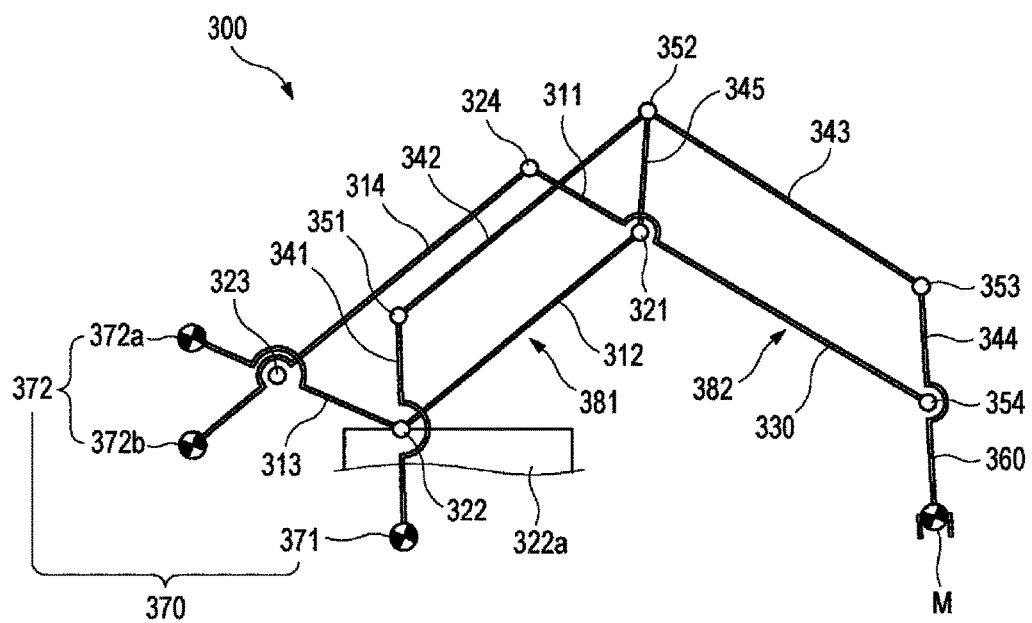
FIG. 10 is a schematic diagram illustrating a stand according to one embodiment of the present disclosure.
Figure 11:
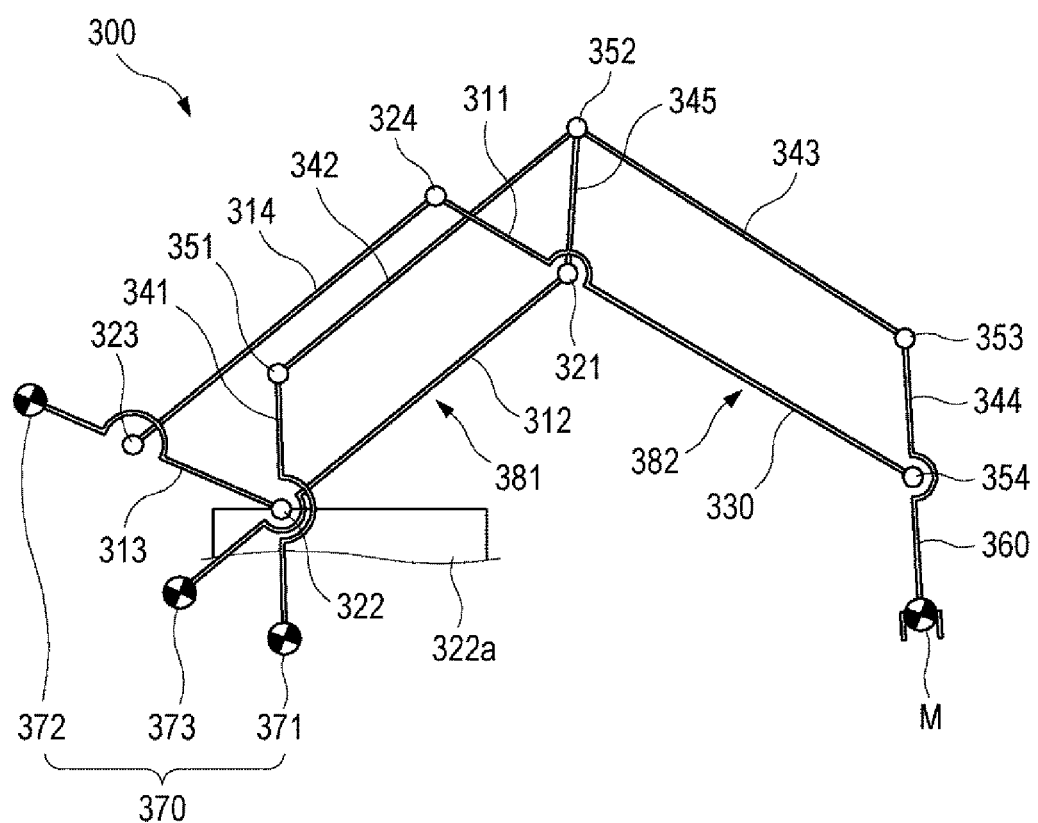
FIG. 11 is a schematic diagram illustrating a stand according to a further embodiment of the present disclosure.
Figure 12:
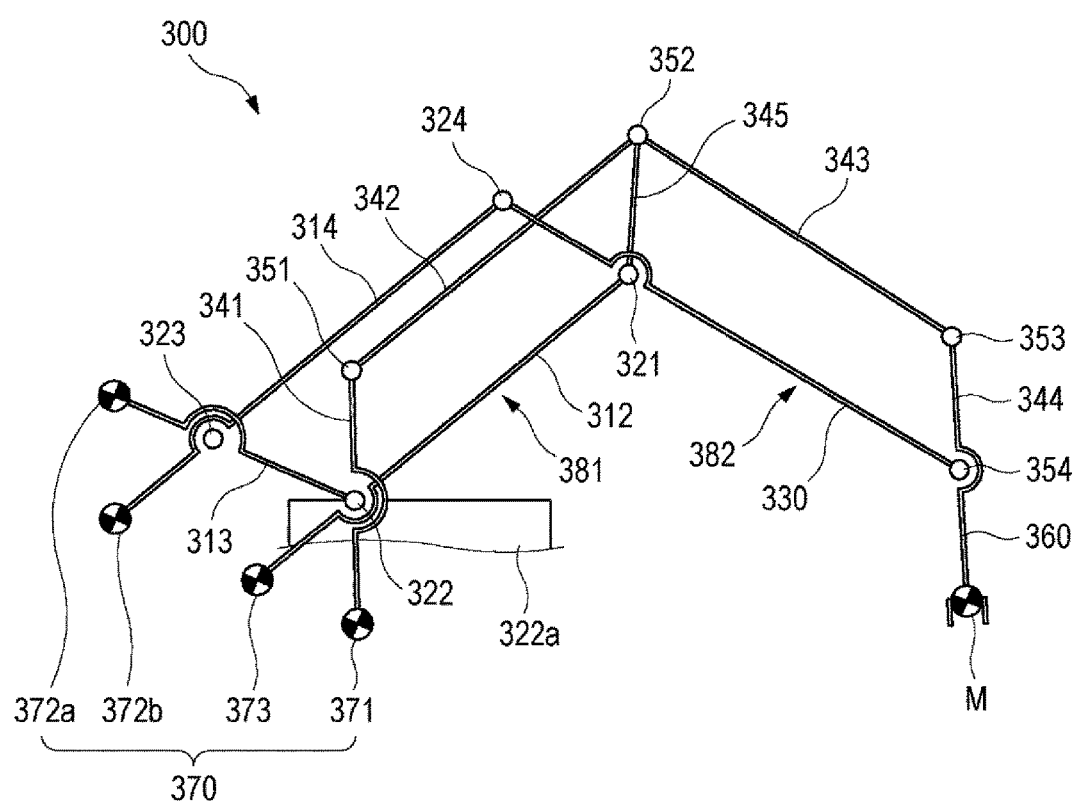
FIG. 12 is a schematic diagram illustrating a stand according to another embodiment of the present disclosure.

FIGS. 10 to 12 are schematic diagrams illustrating stands according to embodiments of the present disclosure, respectively. Referring to FIGS. 10 to 12, the stand 300 according to one embodiment of the present disclosure may include first to fourth links 311, 312, 313, and 314, first to fourth joints 321, 322, 323, and 324, a front link 330, first to fifth extension links 341, 342, 343, 344, and 345, and first to fourth extension joints 351, 352, 353, and 354.

In one embodiment, as shown in FIGS. 10 to 12, the first to fourth links 311, 312, 313, and 314 may be arranged in a parallelogram configuration. Each connection parts of the first to fourth links 311, 312, 313, and 314 may be rotatably connected to one another via each of the first to fourth joints 321, 322, 323, and 324. For example, the first link 311 may be rotatably connected to the second link 312 via the first joint 321. The second link 312 may be rotatably connected to the third link 313 via the second joint 322. The third link 313 may be rotatably connected to the fourth link 314 via the third joint 323. The fourth link 314 may be rotatably connected to the first link 311 via the fourth joint 324.

In one embodiment, as shown in FIGS. 10 to 12, the second joint 322 may be fixed to a holding unit 322a. By way of example, the holding unit 322a may include a part of the stand 300. By way of another example, the holding unit 322a may include a portion of a floor, a wall surface or a ceiling where the stand 300 may be installed.

In one embodiment, as shown in FIGS. 10 to 12, in the parallelogram configuration, the first link 311 and the third link 313 may be arranged on opposite sides, and the second link 312 and the fourth link 314 may be arranged on other opposite sides. In the parallelogram configuration, the second joint 322 and the fourth joint 324 may be arranged in a diagonal direction, and the first joint 321 and the third joint 323 may be arranged in another diagonal direction. The front link 330 may be extended from the first link 311 in a direction from the fourth joint 324 toward the first joint 321. The front link 330 may be rotatable about the first joint 321 together with the first link 311. The first extension link 341 may be rotatably connected to the second joint 322. The first extension joint 351 may be arranged at an end of the first extension link 341. Thus, the first extension link 341 may be arranged between the second joint 322 and the first extension joint 351. The second extension link 342 may be rotatably connected to the first extension joint 351. The second extension joint 352 may be arranged at an end of the second extension link 342. Thus, the second extension link 342 may be arranged between the first extension joint 351 and the second extension joint 352. The third extension link 343 may be rotatably connected to the second extension joint 352. The third extension joint 353 may be arranged at an end of the third extension link 343. Thus, the third extension link 343 may be arranged between the second extension joint 352 the third extension joint 353. The fourth extension joint 354 may be arranged at an end of the front link 330. The fourth extension link 344 may be arranged between the third extension joint 353 and the fourth extension joint 354. The fifth extension link 345 may be arranged between the first joint 321 and the second extension joint 352. The front link 330 may be arranged between the first joint 321 and the fourth extension joint 354.

In one embodiment, as shown in FIGS. 10 to 12, the first extension link 341, the fourth extension link 344, and the fifth extension link 345 may be in parallel with one another. Thus, the stand 300 may include a first parallelogram structure 381 and a second parallelogram structure 382. The first parallelogram structure 381 may be formed by the second link 312, the first extension link 341, the second extension link 342, and the fifth extension link 345. The second parallelogram structure 382 may be formed by the fifth extension link 345, the third extension link 343, the fourth extension link 344, and the front link 330. Thus, the first parallelogram structure 381 and the second parallelogram structure 382 may have the fifth extension link 345 as a common link of the first parallelogram structure 381 and the second parallelogram structure 382. The first parallelogram structure 381 and the second parallelogram structure 382 may be coupled to each other to be symmetrical via the fifth extension link 345. Since the first extension link 341, the fourth extension link 344, and the fifth extension link 345 are in parallel with one another and the fifth extension link 345 serves as the common link of the first parallelogram structure 381 and the second parallelogram structure 382, the stand 300 is capable of always maintaining two parallelogram structures of the first parallelogram structure 381 and the second parallelogram structure 382. Thus, the stand 300 is capable of having a stable state at any rotational angle without requiring additional components to the joints or the links.

In one embodiment, as shown in FIGS. 10 to 12, the stand 300 may further include an extension front link 360 extended from the fourth extension link 344. A predetermined apparatus M may be mounted to an end of the extension front link 360. For example, the predetermined apparatus M may include a medical apparatus. By way of another example, the predetermined apparatus M may be mounted to the front link 330 or the fourth extension link 344. The extension front link 360 may be rotatable with respect to the third extension joint 353 and the fourth extension joint 354 together with the fourth extension link 344.

In one embodiment, as shown in FIGS. 10 to 12, the stand 300 may further include a counterbalance unit 370 having counterweights which are connected to the second joint 322 and the third joint 323, respectively. As a weight of the apparatus M mounted to the extension front link 360 changes, the front link 330 and the fourth extension link 344 may be moved or rotated, thus breaking an initial balance of the stand 300. To restore the balance of the stand 300, a torque in each of the second joint 322 and the third joint 323 must be compensated. In one embodiment, as shown in FIGS. 10 to 12, the counterbalance unit 370 may include a first counterweight 371 connected to the second joint 322 and a second counterweight 372 connected to the third joint 323. The first counterweight 371 can compensate for the torque in the second joint 322 caused by the movements of the front link 330 and the fourth extension link 344. The second counterweight 372 can compensate for the torque in the third joint 323 caused by the movements of the front link 330 and the fourth extension link 344.

Referring to FIGS. 10 to 12, the first counterweight 371 may be extended from the first extension link 341. As the initial balance of the stand 300 is broken, the first extension link 341 may be pivoted or rotated. The first counterweight 371 can compensate for the torque in the second joint 322 caused by the pivot or rotation of the first extension link 341. The second counterweight 372 may be extended from at least one of the third link 313 or the fourth link 341. The second counterweight 372 can compensate for the torque in the third joint 323 caused by the pivot or the rotation of the front link 330. Referring to the example shown in FIG. 11, the second counterweight 372 may be extended from any one of the second link 313 and the fourth link 314. Referring to the examples shown in FIGS. 10 and 12, the second counterweight 372 may include a first weight 372a extended from the third link 313 and a second weight 372b extended from the fourth link 314. Since the second counterweight 372 includes the first weight 372a and the second weight 372b, the torque in the third joint 323 can be compensated by the first weight 372a and the second weight 372b.

In one embodiment, as shown in FIGS. 11 and 12, the counterbalance unit 370 may further include a third counterweight 373 which is connected to the second joint 322 and is extended from the second joint 322 or the second link 312. The third counterweight 373 can compensate for the torque in the second joint 322 caused by the pivot or the rotation of the second link 312. Since the counterbalance unit 370 includes the first counterweight 371 and the third counterweight 373 in the vicinity of the second joint 322, the torque in the second joint 322 can be compensated by the first counterweight 371 and the third counterweight 373.

What is claimed is:

1. A stand, comprising:
    a first link, a second link, a third link, and a fourth link arranged in a parallelogram configuration, the first link and the third link being arranged on opposite sides;
    a first joint, a second joint, a third joint, and a fourth joint to which each connection part of the first link, the second link, the third link, and the fourth link is rotatably connected respectively, the second joint being fixed to a holding unit and the second joint and the fourth joint being arranged in a diagonal direction in the parallelogram configuration;
    a front link extended from the first link in a direction from the fourth joint toward the first joint;
    a first extension link rotatably connected to the second joint;
    a first extension joint arranged at an end of the first extension link;
    a second extension link rotatably connected to the first extension joint;
    a second extension joint arranged at an end of the second extension link;
    a third extension link rotatably connected to the second extension joint;
    a third extension joint arranged at an end of the third extension link;
    a fourth extension joint arranged at an end of the front link;
    a fourth extension link arranged between the third extension joint and the fourth extension joint; and
    a fifth extension link arranged between the first joint and the second extension joint,
    wherein the first extension link, the fourth extension link and the fifth extension link are in parallel with one another.

2. The stand of claim 1, further comprising an extension front link extended from the fourth extension link, wherein a predetermined apparatus is mounted to a tip of the extension front link.

3. The stand of claim 1, further comprising a counterbalance unit which includes counterweights connected to the second joint and the third joint respectively,
    wherein the counterweights compensate torques in the second joint and the third joint respectively, the torques being caused by a movement of the front link and a movement of the fourth extension link.

4. The stand of claim 3, wherein the counterweight connected to the second joint compensates a torque caused by a rotation of the first extension link, and
    wherein the counterweight connected to the third joint compensates a torque caused by a rotation of the front link.

5. The stand of claim 3, wherein the counterweight connected to the second joint is extended from the first extension link and compensates the torque caused by the rotation of the first extension link, and
    wherein the counterweight connected to the third joint is extended from at least one of the third link and fourth link and compensates the torque caused by the rotation of the front link.

6. The stand of claim 5, wherein the counterbalance unit further includes a counterweight which is connected to and is extended from the second joint and compensates a torque caused by a rotation of the second link.

* * * * *